United States Patent [19]

Kato et al.

[11] Patent Number: 5,221,768
[45] Date of Patent: Jun. 22, 1993

[54] PROCESS FOR THE PRODUCTION OF DEUTERATED ACID OR DEUTERATED METHACRYLIC ACID

[75] Inventors: Masaaki Kato; Tetsuya Uno; Masao Kobayashi; Naoto Osuga, all of Otake, Japan

[73] Assignee: Mitsubishi Rayon Co., Ltd., Tokyo, Japan

[21] Appl. No.: 522,418

[22] Filed: May 7, 1990

Related U.S. Application Data

[63] Continuation of Ser. No. 363,798, Jun. 9, 1989, abandoned, which is a continuation of Ser. No. 228,838, Aug. 3, 1988, abandoned, which is a continuation of Ser. No. 867,839, May 28, 1986, abandoned.

[30] Foreign Application Priority Data

May 29, 1985 [JP] Japan .................................. 60-113963
Jun. 30, 1985 [JP] Japan .................................. 60-118800

[51] Int. Cl.$^5$ .............................................. C07C 57/02
[52] U.S. Cl. .................................................. 562/598
[58] Field of Search ......................................... 562/598

[56] References Cited

PUBLICATIONS

Tetrahedron Letters, No. 15, 1961, pp. 516–522.
Journal of the Chemical Society Chemical Communications, No. 23, 1975, pp. 930–932.
Chemical Abstracts, vol. 76, 1972, 156509c.
Journal of Polymer Science, 62, S95 (1962).
Tetrahedron Letters, vol. 23, 3819–3822 (1982), Lockley.
Synthesis and Application of Isotopically Labelled Compounds. Proceedings of International Symposium, 1982, pp. 427–428, Lockley.

*Primary Examiner*—Jose G. Dees
*Assistant Examiner*—Joseph M. Conrad
*Attorney, Agent, or Firm*—Armstrong, Westerman, Hattori, McLeland & Naughton

[57] ABSTRACT

In accordance with the present invention, there is provided a process for the production of deuterated acrylic acid or deuterated methacrylic acid comprising the exchange of hydrogens in acrylic acid or methacrylic acid with deuteriums in the presence of a catalyst. The deuterated acrylic or methacrylic acid is very useful as a starting material in the production of high quality optical plastic fibers.

5 Claims, No Drawings

5,221,768

PROCESS FOR THE PRODUCTION OF DEUTERATED ACID OR DEUTERATED METHACRYLIC ACID

This application is a continuation of application Ser. No. 363,798 filed Jun. 9, 1989, now abandoned which is a continuation of application Ser. No. 228,838 filed Aug. 3, 1988, now abandoned which is a continuation of application Ser. No. 867,839 filed May 28, 1986, now abandoned.

TECHNICAL FIELD

This invention relates to a process for the production of deuterated acrylic acid or deuterated methacrylic acid.

PRIOR ART

Although methods for the production of deuterated methacrylic acid have been hardly known, a method for the production of deuterated methyl methacrylate via deuterated acetone cyanohydrin has been proposed by the Journal of Polymer Science 62, S95 (1962). Thus, a method may be conceived in which deuterated methacrylic acid is obtained by the hydrolysis of deuterated methacrylamide which is an intermediate in the method. The method consists of preparing deuterated acetone cyanohydrin from deuterated acetone and hydrocyanic acid, treating this with sulfuric acid to form the sulfate of methacrylamide, then hydrolyzing this sulfate with heavy water to give deuterated methacrylic acid. However in this method, the use of deuterated starting materials such as deuterated acetone and heavy water has proven economically unsatisfactory because of the large of reaction steps involved. Further, as the related prior art, W. J. S. Lockley has set forth "Regioselective Deuteration of Aromatic and $\alpha,\beta$-unsaturated carboxylic acid" in "Tetrahedron Letters" Vol. 23, 3819–3822 (1982) and also "Regioselective Hydrogen Isotope Exchange Labelling of Aromatic and $\alpha,\beta$-Unsaturated Acids" in "Synthesis and Application of Isotopically Labelled Compounds. Proceedings of an International Symposium 1982" on pages 427–428 which was published in 1983. Particularly, concerning $\alpha,\beta$-unsaturated carboxylic acids, it is disclosed there that $\beta$-deuterated $\alpha,\beta$ unsaturated carboxylic acids can be obtained using rhodium (III) chloride as a catalyst. In said references, however, the selective deuterium substitution on the position of hydrogen attached to $\beta$-carbon of double bond is characterized, and it is merely mentioned there that a polysubstitution reaction will very slightly occur only in case of crotonic acid and cinnamic acid, but no MAA is referred to there. However, the present invention aims at substitution of as many as possible hydrogens in AA or MAA, with deuteriums, which may be attained effectively and economically in accordance with the method of the present invention. For this reason, an improved method involving fewer steps has been sought.

SUMMARY OF THE INVENTION

After extensive research on efficient and practical methods for the production of deuterated methacrylic acid, we discovered a novel manufacturing process involving the direct substitution of hydrogens in methacrylic acid with deuterium, which led us ultimately to the present invention.

According to the present invention, there is provided a process for the manufacture of deuterated acrylic acid or deuterated methacrylic acid comprising the substitution of deuterium for hydrogens in acrylic acid or methacrylic acid in the presence of a catalyst.

DETAILED DESCRIPTION OF THE INVENTION

As the deuterium source for the substitution of deuteriums for hydrogens in acrylic acid or methacrylic acid, heavy water or a mixture of heavy water and deuterium gas may be employed. At least a stoichiometric amount of deuterium with respect to the acrylic acid or methacrylic acid must be present within the reaction system.

Referring to the catalyst, compounds involving palladium, ruthenium, iridium and/or platinum, for example hexachloroiridic acid, tetrakis(triphenylphosphine)-palladium, potassium bromoplatinate, potassium pentachlororuthenate, palladium nitrate, potassium hexahydroxoplatinate and the like are preferred. A mixture of two or more thereof may also be employed.

Referring to another catalyst, compounds involving rhodium and other platinum group elements may be employed. Preferably, rhodium metal may be supported on a suitable carrier such as active carbon or the like. As compounds involving rhodium, sodium hexachlororhodate, chlorotris (triphenylphosphine)rhodium, rhodium chloride and the like are preferred. As compounds involving such platinum group element, there are listed platinum, iridium, palladium, ruthenium or osmium per se and nitrate, chloride, complex compounds or the like thereof, and more concretely, hexachloroiridic acid, tetrakis-(triphenylphosphine)palladium, potassium bromoplatinate, palladium nitrate, potassium hexahydroxoplatinate, potassium tetrachloroplatinate or the like is preferred. Where necessary, these compounds may also be supported on a suitable carrier such as alumina, silica, silica-alumina, diatomaceous earth, active carbon, or the like.

The reaction may be conducted either in a gaseous phase or a liquid phase, and under the application of pressure. To inhibit polymerization during the reaction, a suitable polymerization inhibitor such as phenothiazine, hydroquinone or the like may be added as required. Polymerization may also be inhibited by allowing a small amount of oxygen to be present in the reaction mixture.

In the case of carrying out the present invention, acrylic acid or methacrylic acid is allowed to react with the deuterium source, for example heavy water to substitute deuteriums for hydrogens in acrylic acid or methacrylic acid.

Where necessary, the present reaction is carried out in the presence of a solvent which is stable at the reaction temperature, for example dimethylacetamide, dimethylformamide or the like, and at from room temperature to 300° C., but a temperature from 60° to 200° C. is preferable, especially preferable from 80 to 150° C., from the standpoint of reaction rate as well as the inhibition of side reactions and polymerization. The reaction time is normally from 20 minutes to 100 hours.

The resulting deuterated acrylic acid or deuterated methacrylic acid which can be obtained in accordance with the present invention may be subject to the esterification reaction with alcohol, for example, methylalcohol or deuterated methylalcohol to obtain deuterated methyl acrylate or deuterated methyl methacrylate, respectively, which are used as materials of low light loss optical plastic fibers. Optical plastic fibers made of undeuterated methylmethacrylate or undeuterated methyl acrylate are significantly affected by the vibration absorption of the C-H bonds at the light transmission wavelength, so that it is difficult to make low light loss fibers. However, the conversion of the C-H bonds to C-D bonds by the deuteration removes the influence of C-H vibration absorption, thereby improving the light transmission ability of fibers. By this reason, the best results may be attained when all the C-H bonds have been converted to the C-D bonds, but even in case of a partial deuteration, the effects will be exerted in response to the degree of deuteration.

PREFERRED EMBODIMENTS OF THE INVENTION

In the following Examples, all references to "parts" signify parts by weight. Analyses were conducted by means of a gas chromatograph and a mass spectrometer. The deuteration ratio and the conversion ratio are defined as follows:

$$\text{Deuteration ratio} = \frac{\text{Number of deuterium atoms in deuterated acrylic acid or deuterated methacrylic acid product}}{\text{Number of hydrogen atoms in acrylic acid or methacrylic acid starting material}} \times 100$$

$$\text{Conversion ratio} = \frac{\text{Number of moles of acrylic acid or methacrylic acid reaction product}}{\text{Number of moles of acrylic acid or methacrylic acid charged}} \times 100$$

EXAMPLE 1

8.6 parts of methacrylic acid, 40 parts of heavy water, 0.3 parts of hexachloroiridate, and a trace of hydroquinone as the polymerization inhibitor were placed in a small autoclave and reacted for 24 hours at 110° C. under stirring. After cooling, the reaction product was analyzed and found to be deuterated methacrylic acid with a conversion ratio of 100% and a deuteration ratio of 26%.

EXAMPLE 2

The same process was carried out as in Example 1, except that the 0.3 parts of hexachloroiridate was replaced with 0.58 parts of tetrakis(triphenylphosphine)-palladium. This gave deuterated methacrylic acid with a conversion ratio of 100% and a deuteration ratio of 84%.

EXAMPLE 3

7.2 parts of acrylic acid, 40 parts of heavy water, 1.4 parts of sodium hexachloroiridate, 22 parts of dimethyl acetamide, and a trace of hydroquinone were placed in a flask fitted with a condenser and reacted for 60 hours at 90° C. under stirring. This gave deuterated acrylic acid with a conversion ratio of 79% and a deuteration ratio of 25%.

EXAMPLES 4-9

These reactions were carried out as in Example 1 except that as the catalyst there were used 0.38 parts of potassium bromoplatinate (Example 4), 0.2 parts of potassium pentachlororuthenate (Example 5), 0.23 parts of palladium nitrate (Example 6), 0.2 parts of potassium hexahydroxoplatinate (Example 7), 2 parts of the catalyst of each 1% of palladium and ruthenium supported on active carbon powder (Example 8) or 2 parts of the catalyst of each 1% of palladium and rhodium supported on active carbon powder (Example 9) and further reaction temperature and time were changed as shown in the following Table. The results are given in the following Table.

| Ex- amples | Catalyst | Reaction Temp. (°C.) | Time (hrs.) | Conversion Ratio (%) | Deuteration Ratio (%) |
|---|---|---|---|---|---|
| 4 | Potassium bromoplatinate | 100 | 24 | 70 | 37 |
| 5 | Potassium pentachlororuthenate | 100 | 24 | 82 | 34 |
| 6 | Palladium nitrate | 110 | 24 | 76 | 22 |
| 7 | Potassium hexahydroxoplatinate | 110 | 24 | 99 | 40 |
| 8 | Pd—Ru-active carbon | 90 | 40 | 55 | 25 |
| 9 | Pd—Rh-active carbon | 110 | 16 | 85 | 34 |

EXAMPLE 10

4.3 parts of methacrylic acid, 40 parts of heavy water, 0.1 part of sodium hexachlororhodate, 0.1 part of potassium tetrachloroplatinate and a trace of hydroquinone as the polymerization inhibitor were placed into a small autoclave and reacted for 24 hours at 100° C. under stirring. This gave deuterated methacrylic acid with a conversion ratio of 100% and a deuteration ratio of 65%.

We claim:

1. A process for producing multi-deuterated methacrylic acid comprising reacting methacrylic acid with a source of deuterium atoms in the presence of a tetrakis(triphenylphosphine) palladium catalyst, to substitute deuterium atoms for hydrogen atoms in said methacrylic acid in a deuteration ratio of at least 22% and a conversion ration of at least 55%.

2. A process for producing multi-deuterated methacrylic acid comprising reacting methacrylic acid with a source of deuterium atoms in the presence of a potassium bromoplatinate catalyst, to substitute deuterium atoms for hydrogen atoms in said methacrylic acid in a deuteration ratio of at least 22% and a conversion ration of at least 55%.

3. A process for producing multi-deuterated methacrylic acid comprising reacting methacrylic acid with a source of deuterium atoms in the presence of a palladium nitrate catalyst, to substitute deuterium atoms for hydrogen atom sin said methacrylic acid in a deuteration ratio of at least 22% and a conversion ration of at least 55%.

4. A process for producing multi-deuterated methacrylic acid comprising reacting methacrylic acid with a source of deuterium atoms in the presence of a potassium hexahydroxoplatinate catalyst, to substitute deuterium atoms for hydrogen atoms in said methacrylic acid in a deuteration ratio of at least 22% and a conversion ration of at least 55%.

5. A process for producing multi-deuterated methacrylic acid comprising reacting methacrylic acid with a source of deuterium atoms in the presence of a Pd-Ru-active carbon catalyst, to substitute deuterium atoms for hydrogen atoms in said methacrylic acid in a deuteration ratio of at least 22% and a conversion ration of at least 55%.

* * * * *